United States Patent [19]

Corman et al.

[11] Patent Number: 4,764,532

[45] Date of Patent: Aug. 16, 1988

[54] TREATMENT OF HORSES

[75] Inventors: Lourdes Corman; Ian Mayhew, both of Gainesville, Fla.

[73] Assignee: Efamol Limited, Surrey, England

[21] Appl. No.: 883,316

[22] Filed: Jul. 8, 1986

[30] Foreign Application Priority Data

Jul. 10, 1985 [GB] United Kingdom ............... 8517436

[51] Int. Cl.$^4$ ............................................ A61K 31/20
[52] U.S. Cl. .................................................... 514/560
[58] Field of Search ......................................... 514/560

[56] References Cited

U.S. PATENT DOCUMENTS 4,386,062  5/1983  Beadle .................................. 514/654

Primary Examiner—Frederick E. Waddell
Attorney, Agent, or Firm—Nixon & Vanderhye

[57] ABSTRACT

The invention provides a method of treating anhidrosis in horses or other animals wherein the animals are given γ-linolenic acid and/or dihomo-γ-linolenic acid, restoring sweating abilities.

3 Claims, No Drawings

TREATMENT OF HORSES

FIELD OF THE INVENTION

The invention relates broadly to the treatment of horses and other animals.

GENERAL BACKGROUND

In the tropics, a proportion of horses show a disabling inability to sweat, discussed for example by Correa and Calderin J.A.V.M.A. (Journal of the American Veterinary Medicine Association) 149 No. 12 1556-1560 (1966). A number of possible causes are considered but with the conclusion that none is established and treatment must be empirical.

THE INVENTION

We have found a new approach, success of which is as yet not fully explained but has been clearly demonstrated. It lies in giving the horses $\gamma$-linolenic acid (GLA) or dihomo-$\gamma$-linolenic acid (DGLA) for example 10 mg to 100 g per day, restoring sweating abilities and giving improved condition of hair and skin. A feed supplement is convenient but other means of supply including topical application may be used. Other animals, such as cattle, may suffer a similar problem in hot countries and the invention is applicable in this situation also.

GENERAL DISCUSSION

While as noted above the success of the invention is not fully explained it is believed to lie in correcting an insufficiency of essential fatty acids, leading to a structural or functional derangement of the sweat glands themselves and/or of control of the sweating mechanism.

Considering dietary requirements, it is well known, for example, that linoleic acid cannot be made in the mammalian body and so must be taken in the diet. However, it has been generally thought that the body can readily convert linoleic acid and therefore that provided linoleic acid intake is adequate, no lack of the other n-6 acids will be found.

In previous patent applications (for example Published European Patent Application No. A 0 003 407, U.S. Pat. No. 4,273,763; Published European Patent Application No. A 0 004 770; U.S. Pat. No. 4,309,415; Published European Patent Application No. 0 019 423; U.S. Pat. No. 4,388,324) it has, however, been pointed out that the $\Delta^6$ desaturase which converts linoleic acid to $\gamma$-linolenic acid, is not fully effective in a variety of conditions. The administration of $\gamma$-linolenic acid or dihomo-$\gamma$-linolenic acid or both has been suggested and has been successful in treating a variety of clinical conditions primarily in man but also in a veterinary context.

In the above applications attention is primarily paid to the function of essential fatty acids in prostaglandin (PG) metabolism and in particular to their role in securing a proper balance between 1-series and 2-series PGs.

We are, however, becoming increasingly aware of the significance of the essential fatty acids in themselves, in which considerable general interest has been shown in recent years, primarily in the acids of the n-6 series both as such and in relation to prostaglandin metabolism, but also in the acids of the n-3 series. The n-6 acids in particular are required in the body for the structure of membranes in and around cells, being believed to be necessary for maintaining normal flexibility, fluidity and permeability of such membranes.

The pathways of metabolism of the n-6 essential fatty acids and the related n-3 acids sharing, it is believed, common enzymes in the two pathways, are:

| n-6 | n-3 |
|---|---|
| 18:2 $\Delta^{9,12}$ (linoleic acid) | 18:3 $\Delta^{9,12,15}$ ($\alpha$-linolenic acid) |
| $\downarrow$ $\Delta^6$ desaturase | $\downarrow$ |
| 18:3 $\Delta^{6,9,12}$ ($\gamma$-linolenic acid) | 18:4 $\Delta^{6,9,12,15}$ |
| $\downarrow$ elongation | $\downarrow$ |
| 20:3 $\Delta^{8,11,14}$ (dihomo-$\gamma$-linolenic acid) | 20:4 $\Delta^{8,11,14,17}$ |
| $\downarrow$ $\Delta^5$ desaturase | $\downarrow$ |
| 20:4 $\Delta^{5,8,11,14}$ (arachidonic acid) | 20:5 $\Delta^{5,8,11,14,17}$ |
| $\downarrow$ elongation | $\downarrow$ |
| 22:4 $\Delta^{7,10,13,16}$ (adrenic acid) | 22:5 $\Delta^{7,10,13,16,19}$ |
| $\downarrow$ $\Delta^4$ desaturase | $\downarrow$ |
| 22:5 $\Delta^{4,7,10,13,16}$ | 22:6 $\Delta^{4,7,10,13,16,19}$ |

The pathways are not reversible in mammals nor, are n-3 and n-6 series acids interconvertible.

The acids, which naturally are of the all-cis configuration, are systematically named as derivatives of the corresponding octadecanoic, eicosanoic or docosanoic acids e.g. $\Delta^{9,12}$octadecadienoic acid or $\Delta^{4,7,10,13,16,19}$ docosahexaenoic acid, but numerical designation such as, correspondingly, 18:2 n-6 or 22:6 n-3 is convenient. Initials, for example, DHA for 22:6 n-3 (docosahexaenoic acid), are also used but do not serve when n-3 and n-6 acids of the same chain length and degree of unsaturation exist. Trivial names in more or less common use in the n-6 series are as shown. Of the n-3 series only 18:3 n-3 has a commonly used trivial name, $\alpha$-linolenic acid. It was characterised earlier than $\gamma$-linolenic acid and reference in the literature simply to linolenic acid, especially in the earlier literature is to the $\alpha$-acid.

In the body, the n-3 acids are metabolised preferentially and as a result, in plasma for example, levels of $\alpha$-linolenic acid (18:3 n-3) are low and 18:4 n-3 and 20:4 n-3 are in trace amounts only. In contrast the n-6 acids are normally present in moderate amounts, though $\gamma$-linolenic acid (GLA) is at low levels, being apparently converted to diohomo-$\gamma$-linolenic acid (DGLA) more rapidly than its relatively slow production from linoleic acid. In both series the elongation stages in the metabolic pathways are much more rapid than the desaturations.

FURTHER FEATURES OF THE INVENTION

As appears from above the invention is essentially in providing affected animals with GLA or DGLA and may thus be regarded as constituted by GLA or DGLA when prepared as a medicament or feed supplement for horses, cattle or other animals, or by a method of treating equine anhidrosis or similar conditions in other animals wherein affected animals are given an effective amount of GLA or DGLA orally, topically or in any other way, or by a method of preparing a medicament of feedstuff for treatment of such conditions characterised by use of GLA or DGLA as the active material in a conveniently administrable form.

Further, in combination with GLA or DGLA it is advantageous to use other essential fatty acids of the n-6 series. GLA or DGLA would be expected to be converted along the whole pathway but since some of the steps are known to be slow, direct dietary supplementation with one or more of arachidonic acid, adrenic acid and 22:5 n-6 will thus be of value. Further, the effect of GLA or DGLA will be enhanced by adding in one or more of the higher n-3 fatty acids, viz 18:4, 20:4, 20:5, 22:5 and 22:6. Dosages of such all acids are conveniently 10 mg to 100 g/day/kg body weight.

FORMS OF THE ACIDS

The acids may be as such or as pharmaceutically acceptable and physiologically equivalent derivatives as, for example, detailed later herein for GLA and DGLA, and reference to any of the acids, in particular in the claims herein, is to be taken as including reference to the acids when in the form of such derivatives. Equivalence is demonstrated by entry into the pathway quoted herein, as evidenced by effects corresponding to those of the acids themselves or their natrual glyceride esters. Thus, indirect identification of useful derivatives is by their having the valuable effect in the body of the acid itself, but conversion can be shown directly by gas chromatographic analysis of concentrations in blood, body fat, or other tissue by standard techniques, for example those of Pelick et al. p. 23, "Analysis of Lipids and Lipoproteins" Ed. Perkins, American Oil Chemists Society, Champaign, Ill., U.S.A.

In outline the method is suitably that plasma samples (1 ml) are extracted with chloroform:methanol (2:1). The extract is filtered through sodium sulphate, evaporated to dryness, and taken up in 0.5 ml chloroform:methanol. The lipid fractions are separated by thin layer chromatography on silica gel plates. The phospholipid fraction, taken to reflect essential fatty acid contents most sensitively, is methylated using boron trifluoride-methanol. The resulting methyl esters of the fatty acids are separated and measured using a Hewlett-Packard 5880 gas chromatograph with a six foot column packed with 10% silar on chromosorb WAW 106/230. The carrier gas is helium (30 ml/min). Oven temperature is programmed to rise from 165° C. to 190° C. at 2° C./min. Detector temperature is 220° C. and injector temperature 200° C. Retention times and peak areas are automatically computed by Hewlett-Packard Level 4 integrator. Peaks are identified by comparison with standard fatty acid methyl esters.

PACKS

If it is not desired to have compositions comprising different active materials together, packs may be prepared comprising the materials presented for separate, or part joint and part separate administration in the appropriate relative amounts, and use of such packs is within the purview of this invention.

FORMS AND SOURCES OF γ-LINOLENIC AND OTHER ACIDS

Convenient physiologically equivalent derivatives of γ-linolenic acid and dihomo-γ-linolenic acid for use according to the invention, as with other acids, include salts, amides, phospholipids and esters, including glycerides and alkyl (e.g. $C_1$ to $C_4$) esters.

Natural or synthetic acids, as such or as the derivatives may be used in pure form. It is, however, at present convenient to incorporate at least the γ-linolenic acid into compositions in the form of an available oil having a high γ-linolenic acid content, hence references to "oil" herein.

At the present time known natural sources of oils having a high γ-linolenic acid content are few (there are no known natural sources of significant amounts of dihomo-γ-linolenic acid). One source of oils currently available is the seed of Evening Primrose species such as *Oenothera biennis L.* and *Oenothera lamarckiana,* the oil extract therefrom containing γ-linolenic acid (about 8%) and linoleic acid (about 72%) in the form of their glycerides together with other glycerides (percentages based on total fatty acids). Other sources of γ-linolenic acid are Borage species such as *Borago officinalis* which, though current yield per acre is low, provide a richer source of γ-linolenic acid than Oenothera oil. Recent studies on fungi which can be cultivated by fermentation promise a fungal oil source.

The oil is extracted from the seed by one of the conventional methods of extraction such as cold pressure, screw pressure after partially cooking the seed, or solvent extraction.

Fractionation of a typical sample of this oil in the form of methyl esters shows the relative proportions:

| | |
|---|---|
| Palmitate | 6.15 |
| Stearate | 1.6 |
| Oleate | 10.15 |
| Linoleate | 72.6 |
| γ-Linoleate | 8.9 |

As preservative, α-tocopherol is added to the oil in a concentration 0.1%.

The seed oil extracts referred to above can be used as such or can, for example, if desired, be fractionated to yield an oily composition containing the triglycerides of γ-linolenic and linoleic as the main fatty acid components, the γ-linolenic acid content being if desired a major proportion. Seed oil extracts appear to have a stabilising effect upon dihomo-γ-linolenic acid if present.

SOURCES OF OTHER ACIDS

Natural sources of 22:4 and 22:5 n-6 acids include adrenal glands (22:5) and kidneys (22:4) obtained from slaughter houses, and 22:4 in the fat of the American Snapping Turtle. The n-3 acids are available from fish oils, particularly 20:5 n-3 and 22:6 n-3.

The acids can be isolated from these sources by, for example, saponification under mild non-oxidising conditions followed by preparative gas liquid chromatography. Synthesis of the acids is difficult but not impossible and provides another source.

PRESENTATION

The compositions according to the invention, when not feedstuffs, are conveniently in a form suitable for topical, oral, rectal or parenteral administration in a suitable vehicle all in ways conventional per se. Thus, for example, tablets, capsules, ingestible liquid or powder preparations can be prepared as required. Injectable solutions of hydrolysed Oenothera oil may be prepared using albumin to solubilise the free acid.

Advantageously, a preservative is incorporated into the preparations. α-tocopherol in concentration of about 0.1% by weight has been found suitable for the purpose.

It will be understood that the absolute quantity of active materials present in any dosage unit should not exceed that appropriate to the rate and manner of administration to be employed but on the other hand should also desirably be adequate to allow the desired rate of administration to be achieved by a small number of doses.

EXAMPLES OF TREATMENT

Three horses that were chronic anhidrotics were placed on a trial regimen of evening primrose oil (0.5 gm. capsules 4 b.i.d.) and safflower oil (30 gm. b.i.d.) in late summer, in Florida, U.S.A. All three of these animals had an elevated temperature at rest when seen. During the trial vastly improved sweating abilities and improved condition of hair and skin were reported for all three animals throughout the late summer, autumn and winter.

Horse I

Eighteen year old quarter horse mare used for pleasure riding. Always a "non-sweater" since about three years of age. Condition had been getting worse over the years such that the horse could not be used when ambient temperatures were high. On one occasion the previous summer the horse had collapsed in heat stroke after a short period of exercise.

Diet during the trial included sweet feed (12% protein mixed grain feed plus molasses), pellets, grass or coastal Bermuda grass hay, electrolyte and mineral supplement and salt.

One month after treatment began there was improved sweating. The owner had never seen the horse have such a well grown, shiny hair coat which persisted through to the following spring.

Horse II

Eight year old thoroughbred gelding. Non-sweater since at least six years old, though with occasional sweating under mane. Purchased cheaply because of the severe anhidrosis. Diet during the trial consisted of oats, grass hay and iodine/mineral supplement.

Throughout the autumn and winter and into the following spring the horse became drenched in sweat after strenuous exercise and did not fatigue in events that the previous owner could not use him in. Owner commented on improved hair coat.

Horse III

Nine year old thoroughbred gelding. Owned since four years old. Anhidrosis had been worse each year of ownership especially last two years when the horse had been brought into an area where weather is hotter. Diet during the trial was sweet feed, oats, hay and salt.

During late summer while on oil supplement, the horse would sweat over crest of neck and flanks with pleasure riding. This also occurred at rest, something the owner had never seen before, even in hotter weather. With harder exercise the horse still would "puff" (hyperventilate) but would sweat. When dried off there would be a thick crust of salt, that also the owner had never seen before. At this stage the horse was not getting supplemental salt in the feed.

The following are specific Examples of the capsules suitable for use as above.

EXAMPLE 1

A capsule containing 0.3 g Evening Primrose Oil and 0.2 g mackerel oil administered six times per day.

EXAMPLE 2

A capsule containing 0.35 g Evening Primrose Oil and 0.15 g salmon oil administered eight times per day.

EXAMPLE 3

A capsule containing 150 mg of GLA and 100 mg of 20:5 n-3 administered three times per day.

EXAMPLE 4

A capsule containing 50 mg of DGLA, 20 mg of 18:4 n-3, 20 mg of 20:4 n-3, 50 mg of 20:5 n-3, 20 mg of 22:5 n-3 and 20 mg of 22:6 n-3 administered four times per day.

EXAMPLE 5

A capsule containing 0.5 g Evening Primrose Oil administered six times per day.

We claim:

1. A method of treating anhidrosis in horses wherein the animals are given gamma-linolenic acid and/or dihomo-gamma linolenic acid, restoring sweating abilities, wherein the amount of the or each said acid given is 10 mg to 100 g/day.

2. A method according to claim 1, wherein one or more of the 20:4, 22:4 and 22:5 acids of the n-6 series of essential fatty acids is given also.

3. A method according to claim 1, wherein one or more of the 18:3, 18:4, 20:4, 20:5, 22:5 and 22:6 acids of the n-3 series of essential fatty acids is given also.

* * * * *